United States Patent [19]

Scherowsky et al.

[11] Patent Number: 5,334,328
[45] Date of Patent: Aug. 2, 1994

[54] CHIRAL AZETIDINONE DERIVATIVES, AND THEIR USE AS DOPES IN LIQUID-CRYSTAL MIXTURES

[75] Inventors: Günter Scherowsky; Claas Junghans, both of Berlin; Anke Kaltbeitzel, Rüsselsheim; Rainer Wingen, Hattersheim am Main; Britta Michalski, Berlin, all of Fed. Rep. of Germany

[73] Assignee: Hoechst Aktiwengesellschaft, Frankfurt am Main, Fed. Rep. of Germany

[21] Appl. No.: 900,167

[22] Filed: Jun. 17, 1992

[30] Foreign Application Priority Data

Jun. 19, 1991 [DE] Fed. Rep. of Germany ....... 4120220
Jun. 25, 1991 [DE] Fed. Rep. of Germany ....... 4120981

[51] Int. Cl.$^5$ .................... C09K 19/34; C07D 205/08
[52] U.S. Cl. .............................. 252/299.61; 540/357; 540/361; 540/363
[58] Field of Search ................... 252/299.61; 540/357, 540/361, 363

[56] References Cited

FOREIGN PATENT DOCUMENTS 2108664 4/1990 Japan ................................. 540/364
403236371 11/1991 Japan ................................. 540/357

OTHER PUBLICATIONS

Japanese Journal of Applied Physics, Bd. 27, Nr. 12, 1988, Tokyo, pp. L2241-L2244, H. R. Duball, "Three classes of new chiral dopants: Synthesis and Physical Qualifications as Dopants for Practical FLC-Mixtures".

Primary Examiner—Richard D. Lovering
Assistant Examiner—C. Harris
Attorney, Agent, or Firm—Curtis, Morris & Safford

[57] ABSTRACT

Azetidinones of the formula I

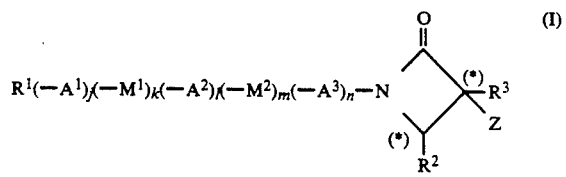

in which, for example, $R^1$ is an alkyl or alkenyl radical, $R^2$ and $R^3$ are hydrogen or an alkyl or alkenyl radical, Z is hydrogen or (pseudo)halogen, $A^1$, $A^2$ and $A^3$ are a ring system, and M is a spacer group, can be added to liquid-crystal mixtures. Even when admixed in small amounts, they cause considerable twist in the cholesteric and smectic C* phase, which can compensate the pitch of another dope or produce a short $S_C^*$ pitch.

5 Claims, No Drawings

CHIRAL AZETIDINONE DERIVATIVES, AND THEIR USE AS DOPES IN LIQUID-CRYSTAL MIXTURES

DESCRIPTION

In particular in the last decade, liquid crystals have found their way into various industrial areas in which electro-optical and display-device properties are required (for example in watch, calculator and typewriter displays). These display devices are based on the dielectric alignment effects in the nematic, cholesteric and/or smectic phases of the liquid-crystalline compounds, where, due to the dielectric anistropy, the molecular long axes of the compounds adopt a preferential alignment in an applied electrical field. The usual response times in these display devices are too long for many other potential areas of application of liquid crystals. This disadvantage is particularly noticeable if a large number of pixels must be addressed. The production costs of equipment containing relatively large screen surfaces, such as, for example, video equipment, are then generally too high.

In addition to nematic and cholesteric liquid crystals, optically active smectic liquid-crystal phases have also been increasing in importance for a few years.

Clark and Lagerwall were able to show that the use of ferroelectric liquid-crystal systems in very thin cells gives opto-electrical switching or display elements which have response times faster than conventional TN ("twisted nematic") cells by a factor of up to 1,000 (cf., for example, Lagerwall et al., "Ferroelectric Liquid Crystals for Displays", SID Symposium, October Meeting, 1985, San Diego, Calif., USA). Due to these and other favorable properties, for example the possibility for bistable switching and the contrast which is virtually independent of the viewing angle, FLCs are in principle suitable for the abovementioned areas of application, for example via matrix addressing. Electro-optical switching and display elements require either compounds which form tilted or orthogonal smectic phases and are themselves optically active, or ferro-electric smectic phases can be induced in compounds which, although forming smectic phases, are not themselves optically active, by doping with optically active compounds. The desired phase should be stable over the broadest possible temperature range.

In order to achieve good contrast in electro-optical components, a uniform planar alignment of the liquid crystals is necessary. Good alignment in $S^*_A$ and $S^*_C$ phases can be achieved if the phase sequence of the liquid-crystal mixture is, with decreasing temperature:

isotropic→N*→$S^*_A$→$S^*_C$

The prerequisite is that the pitch of the helix in the N* phase is very large (greater than 10 μm) or, even better, is fully compensated (see, for example, T. Matsumoto et al., Proc. of the 6th Int. Display Research Conf., Japan Display, Sept. 30–Oct. 2, 1986, Tokyo, Japan, p. 468–470; M. Murakami et al., ibid., p. 344–347). This is achieved by adding to the chiral liquid-crystal mixture, which has, for example, a left-handed helix in the N* phase, a further optically active dope which induces a right-handed helix, in such amounts that the helix is just compensated.

A further prerequisite for the use of the SSFLCD effect (surface stablilized ferroelectric liquid crystal display) of Clark and Lagerwall for uniform, planar alignment is that the pitch in the smectic C* phase is significantly greater than the thickness of the display element (Mol. Cryst. Liq. Cryst. 94 (1983), 213–314 and 114 (1984), 151–187). This is achieved, as in the case of the cholesteric pitch, by using dopes having the opposite direction of rotation of the helix.

Ferroelectric liquid-crystal displays can also be operated by utilizing the DHF effect or the PSFLCD effect (pitch stabilized ferroelectric liquid crystal display, also known as SBF=short pitch bistable ferroelectric effect). The DHF effect was described by B. I. Ostrovski in Advances in Liquid Crystal Research and Applications, Oxford/Budapest, 1980, 469 ff., and the PSFLCD effect is described in DE 3 920 625 and EP 0 405 346 A2. Utilization of these effects requires, in contrast to the SSFLCD effect, a liquid-crystalline material having a short $S_C$ pitch.

It has now been found that optically active azetidinones as dopes in tilted smectic liquid-crystalline phases result in a high degree of twist in the cholesteric and smectic C* phases, even when added in small amounts. This helix induced in the N* and $S^*_C$ phase can advantageously be used to specifically compensate the pitch or alternatively to produce a short $S_C$ pitch. It is particularly advantageous here that the dopes according to the invention, due to their high twist capacity, cause these effects even when added in small amounts.

The optical response time τ[μs] of ferroelectric liquid-crystal systems, which should be as short as possible, depends on the rotational viscosity of the system γ[mPas], the spontaneous polarization $P_s$[nC/cm²] and the electrical field strength E[V/m], in accordance with the equation $$\tau \sim \frac{\gamma}{P_S \cdot E}$$

Since the field strength E is determined by the electrode separation in the electro-optical component and by the applied voltage, the ferroelectric display medium must have low viscosity and high spontaneous polarization so that a short response time is achieved.

It has been found, surprisingly, that even addition of only a small amount of the substance according to the invention induces high spontaneous polarization in a non-chiral base mixture, so that short response times can be achieved by using this compound.

The invention therefore relates to the use of chiral or optically active azetidinones as dopes in liquid-crystal mixtures. The invention furthermore relates to liquid-crystal systems which contain chiral or optically active azetidinones, and to novel chiral azetidinones (both as optically active compounds and as racemic mixtures). The azetidinones to be employed according to the invention conform to the formula (I)

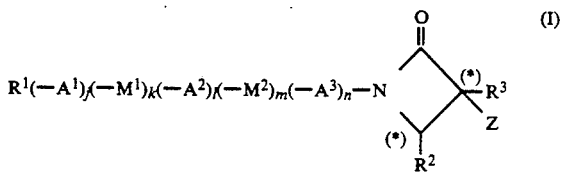

in which the symbols and indices have the following meanings:

(*) indicates a possible chiral center, $R^1$ is a straight-chain or branched alkyl radical having 1 to 16 carbon atoms or a straight-chain or branched alkenyl radical having 3 to 16 carbon atoms in which even asymmetrical carbon atoms may be present, in which one or more non-adjacent —CH$_2$— groups may be replaced by —O—, —S—, —CO—, —O—CO— and/or —CO—O—, which correspondingly reduces the number of carbon atoms in the radical, and in which one or more H atoms may be replaced by F, Cl, Br or CN, $R^2$ is a hydrogen atom or an alkyl radical having 1 to 10 carbon atoms and in which the —CH$_2$— group adjacent to the ring may be replaced by —O— or

which correspondingly reduces the number of carbon atoms in the radical, $R^3$ is a hydrogen atom or an alkyl radical having 1 to 10 carbon atoms, Z is H, F, Cl, NO$_2$ or N$_3$, j and l are 0, 1 or 2, k and m are 0 or 1, and n is 0, 1 or 2, with the following proviso: if j and/or l are zero, k is zero; if n is zero, m is zero; the sum of J+l+n is at least 1 and at most 3, —A$^1$ and —A$^2$ are

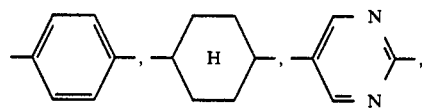
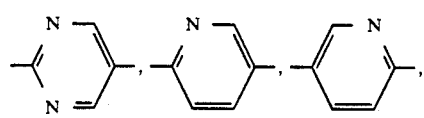
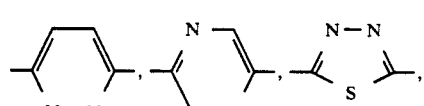
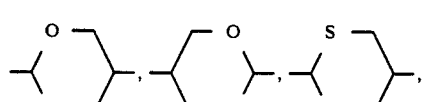
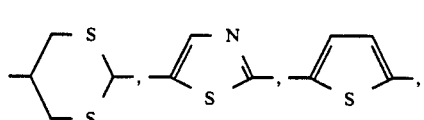
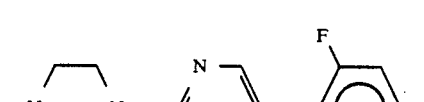
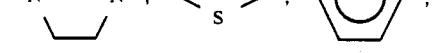

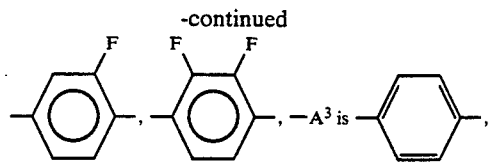, —A$^3$ is

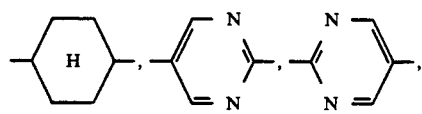

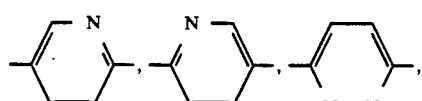

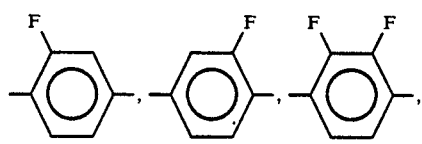

and

—M$^1$ and —M$^2$ are —O—CO—, —CO—O—, —CH$_2$CH$_2$—, —CH=CH—, —CH$_2$—O— or —O—CH$_2$—.

In a preferred embodiment, azetidinones of the formula (I) are employed in which $R^1$ is a straight-chain or branched alkyl or alkenyl radical having 6 to 12 carbon atoms and possibly containing an asymmetrical carbon atom, and in which one —CH$_2$— group may be replaced by —O—, —CO— or —COO—, which correspondingly reduces the number of carbon atoms in the radical, and the (—A$^1$)$_j$(—M$^1$)$_k$(—A$^2$)$_l$(—M$^2$)$_m$(—A$^3$)$_n$— group has the following meaning:

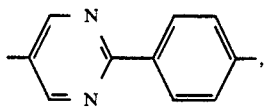

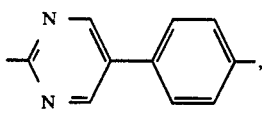

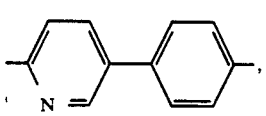

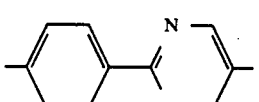

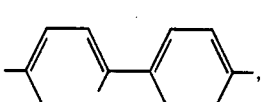

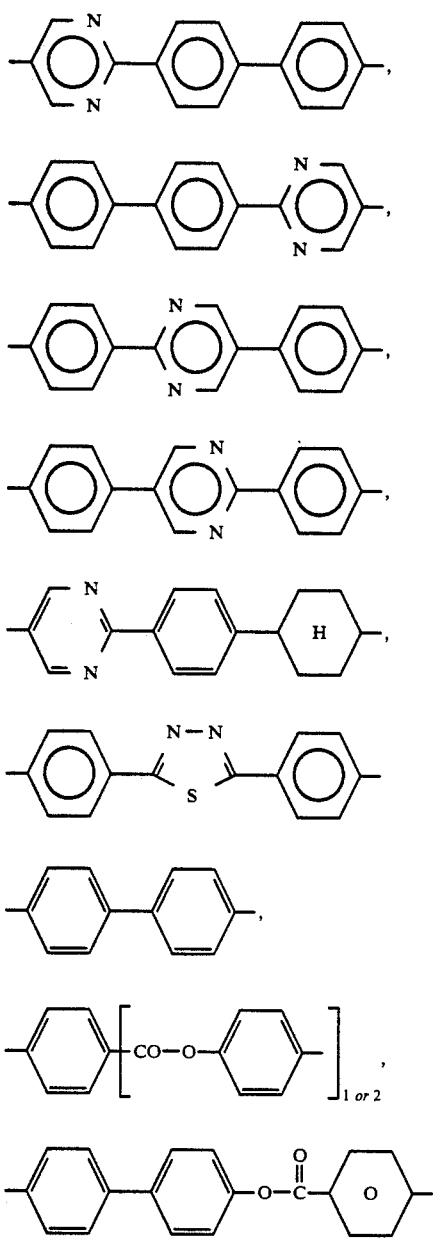

The azetidinones of the formula (I) can be obtained by multistep synthetic routes using individual reactions which are known from the literature. The general preparation methods are discussed in greater detail in the experimental part.

Said azetidinones are suitable as components of liquid-crystal mixtures. The LC mixtures preferably contain from 0.01 to 60% by weight, in particular from 0.1 to 20% by weight, particularly preferably from 0.1 to 5% by weight, of said azetidinones. The other constituents are preferably selected from known compounds having nematic, cholesteric and/or smectic phases; these include, for example, Schiff bases, biphenyls, terphenyls, phenylcyclohexanes, cyclohexylbiphenyls, N-, S- or O-containing heterocyclic compounds, for example pyrimidines, cinnamic acid esters, cholesterol esters or various bridged, polycyclic esters of p-alkylbenzoic acids with terminal polar groups. In general, the commercially available liquid-crystal mixtures, even before addition of the optically active compound(s), are in the form of mixtures of various components, of which at least one is mesogenic, i.e. is a compound which, in derivatized form or mixed with other components, has a liquid-crystal phase which gives rise to expectations of the formation of at least one enantiotropic (clearing point > melting point) or monotropic (clearing point < melting point) mesophase.

The high twist capacity of the compounds according to the invention results in advantageous possible uses, even in nematic phases in the rather "classical" display technologies. Here, however, it is frequently not the compensation, but the achievement of twist by addition of the smallest possible amount of chiral dope that is in the foreground. This applies both to TN ("twisted nematic") technology [see M. Schadt et al., Appl. Phys. Lett. 18, 127 (1971)] and to the White-Taylor display [D. L. White et al., J. Appl. Phys. 45, 4718 (1974)] or the SBE/STN ("super-birefringence effect"/"super-twisted nematic") display [T. J. Scheffer et al., Appl. Phys. Lett. 45, 1021 (1984)] and its various modifications, such as the OMI ("optical mode interference") display [M. Schadt et al., Appl. Phys. Lett. 50, 236 (1987)].

The liquid-crystal mixtures can be employed, for example, in electro-optical switching and display devices, which, in addition, contain the following components, inter alia: two electrodes, two outer plates and at least one alignment layer. The structure of FLC displays is described in general terms in EP-B 0 032 362.

The invention is described in greater detail by the examples below.

The process for the preparation of the compounds of the formula (I) comprises reacting, in accordance with scheme 1, a carboxylic acid of the formula (XIII)—prepared from known starting materials by reactions known in principle from the literature and in which $P_g$ is a protecting group, for example tert.-butyldiphenylsilyl or tert.-butyldimethylsilyl—with a mesogenic amine (XIX)—here, $Y^1$ is a group which can later form $M^2$ with $Y^2$, i.e. is, for example, —OH, —$OP_g$, —$CO_2H$ or —$CO_2R'$—to give an anilide of the formula (XIV). (XIV) is deprotected in a manner which is likewise known from the literature, to give (XV), which is functionalized to give (XVI) and further to give the azetidinone (XVII). Suitable reaction of the functionalities $Y^1$ and $Y^2$ in (XVII) and (XVIII) respectively—for example esterification—gives (I).

If m and k are each zero, i.e. $A^3$ and $A^2$ and/or $A^1$ are linked by single bonds, it is also possible to react the acid (XIII) with the mesogenic amine (XX) in accordance with scheme 2 to give the anilide (XXI). The deprotection (XXII) and functionalization (XXIII) and the ring closure are carried out analogously to scheme 1 to give (I).

Scheme 1
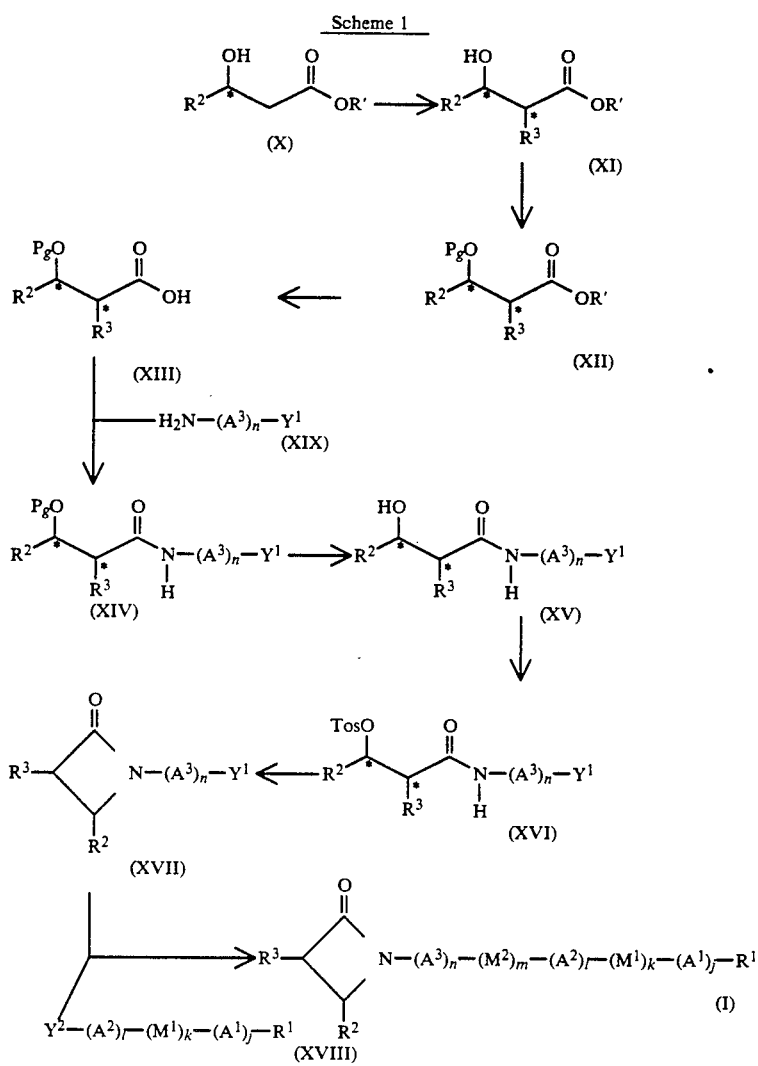
Scheme 2
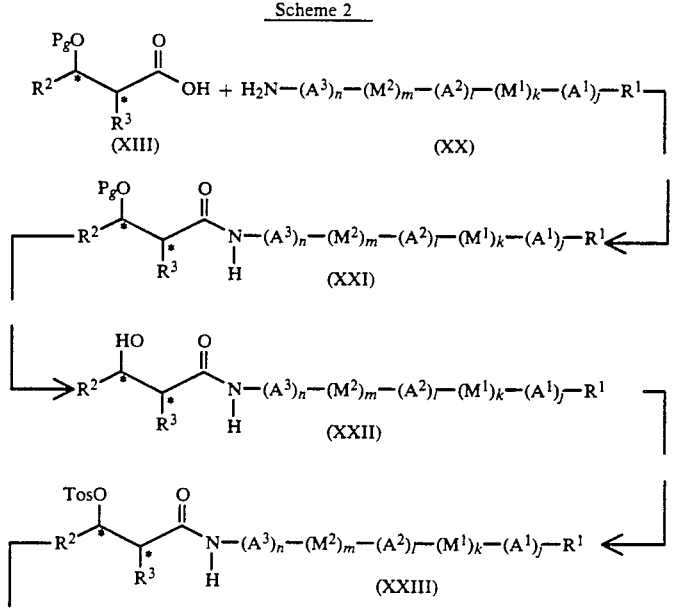

Scheme 2

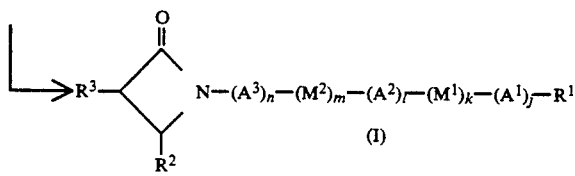

EXAMPLE 1

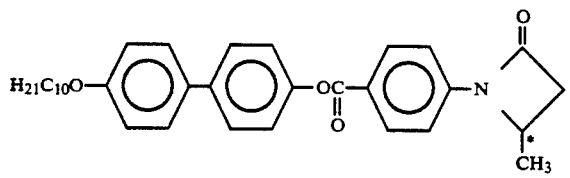

(S)-1-[(4'-Decyloxybiphenyl-4-yl)oxycarbonylphenyl]-4-methylazetidin-2-one.

18.25 g of ethyl (R)-3-tert.-butyldiphenylsilyloxybutanoate—obtained by reacting ethyl (R)-3-hydroxybutanoate with tert.-butyldiphenylchlorosilane and imidazole in dimethylformamide—are stirred for 70 hours at room temperature with a solution of 6.4 g of potassium hydroxide in 100 ml of ethanol. Work-up gives 13.7 g of (R)-3-tert.-butyldiphenylsilyloxybutanoic acid of melting point 103° C. and of $[α]_D^{20}$ 1.3° (c=16.9, CHCl$_3$).

A solution of 4.48 g of (R)-3-tert.-butyldiphenylsilyloxybutanoic acid in 10 ml of toluene is treated with twice the molar amount of oxalyl chloride, and the mixture is heated at the boil for 1 hour. The volatile components are removed by distillation, the residue is taken up in 10 ml of dichloromethane, and this solution is added dropwise to a solution of 2.98 g of benzyl 4-aminobenzoate and 5 ml of triethylamine in 15 ml dichloromethane. Aqueous work-up, extraction with diethyl ether and chromatographic purification (silica gel, hexane/diethyl ether 1:1) give 5.98 g of 4'-benzyloxycarbonyl-(R)-3-(t-butyldiphenylsilyloxy)butanilide as a colorless oil of $[α]_D^{20}$ −2.3° (c=10.9, CHCl$_{34}$). 18 ml of a 1.1M solution of tetrabutylammonium chloride in tetrahydrofuran are added dropwise to a solution of 5.17 g of 4'-benzyloxycarbonyl-(R)-3-(tert-butyldiphenylsilyloxy)butanilide in 7 ml of tetrahydrofuran. Appropriate work-up and chromatic purification give 1.35 g of 4'-benzyloxycarbonyl-(R)-3-hydroxybutanilide of melting point 114° C. and $[α]_D^{20}$ of −26.4° (c=9.1, CHCl$_3$).

1 g of 4-toluenesulfonyl chloride is added to a solution of 1.02 g of 4'-benzyloxycarbonyl-(R)-3-hydroxybutanilide in 4 ml of pyridine. Customary work-up and chromatographic purification give 1.27 g of 4'-benzyloxycarbonyl(R)-3-(4-methylphenylsulfonyloxy)butanilide of melting point 87° C.

2.44 g of 4'-benzyloxycarbonyl-(R)-3-(4-methylphenylsulfonyloxy)butanilide are added at 5° C. over the course of 3 hours to a suspension of 170 mg of sodium hydride in 60 ml of dichloromethane/dimethylformamide (4:1). After a further hour, 40 ml of saturated ammonium chloride solution are added. The organic phase is evaporated to dryness in vacuo, the residue is taken up in 50 ml of diethyl ether, and the solution is washed three times with 20 ml of water in each case. Evaporation and recrystallization from diethyl ether/hexane mixtures give 1.44 g of (S)-1-(4-benzyloxycarbonylphenyl)-4-methyl-azetidin-2-one of melting point 89° C.

A solution of 700 mg of (S)-1-(4-benzyloxycarbonylphenyl)-4-methylazetidin-2-one in 25 ml of methanol is hydrogenated using 70 mg of Pd/C (10%). Work-up gives 0.455 g of (S)-1-(4-carboxy)phenyl-4-methylazetidin-2-one of melting point 162° C. and $[α]_D^{20}$ of 68.2° (c=7.1, CHCl$_3$).

750 mg of 4-decyloxy-4'-hydroxybiphenyl, 515 mg of dicyclohexylcarbodiimide and 40 mg of 4-dimethylaminopyridine are added to a solution of 455 mg of (S)-1-(4-carboxy)phenyl-4-methylazetidin-2-one in 3 ml of dichloromethane and 3 ml of dimethylformamide. Customary work-up and chromatic purification give 350 mg of crude product, which are recrystallized twice from diethyl ether/hexane mixtures.

Phase sequence: X$_1$ 110 X$_2$ 115 S$_x$ 118 N* 174 I

The following compounds are obtained analogously or using methyl (2R,3R)-2-octyl-3-hydroxybutanoate (obtained from methyl 3-hydroxybutanoate by the method of G. Fratér, Helv. Chem. Acta 62, 2829 (1979)) and ethyl (R)-3-hydroxy-2-methylpropanoate.

EXAMPLE 2

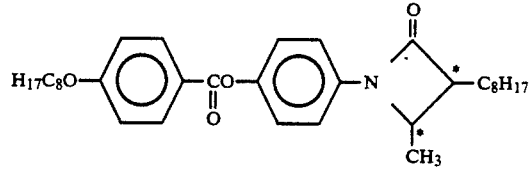

Phase sequence X 69 S$_C$* 101 S$_A$* 106 N* 128 I

EXAMPLE 3

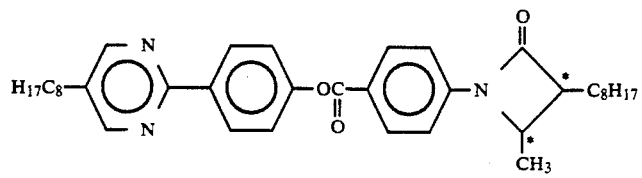

Phase sequence X 82 N* 212 I [α]$_D^{20}$: 21.2° (c=3.4, CHCl₃)

EXAMPLE 4

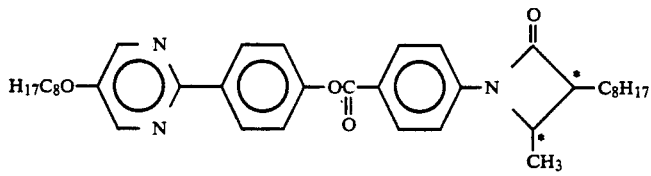

Phase sequence X₁ 93 X₂ 102 S$_C$* 121 N* 230 I

EXAMPLE 5

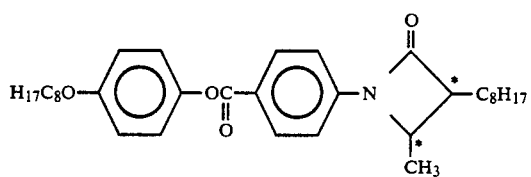

Phase sequence X 79 S$_C$* 84 S$_A$ 133.7 N* 144.0 I
[α]$_D^{20}$: 31.9° (c=1.9, CHCl₃)

EXAMPLE 6

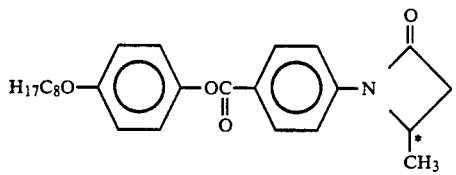

Melting point: 100° C.

EXAMPLE 7

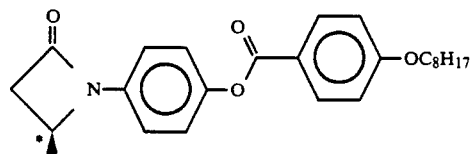

Melting point: 108° C. [α]$_D^{22}$: +33.8° (c=1.1; CHCl₃)

EXAMPLE 8

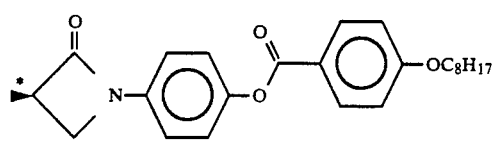

Melting point: 125° C. [α]$_D^{23}$: +1.6° (c=1.2; CHCl₃)

EXAMPLE 9

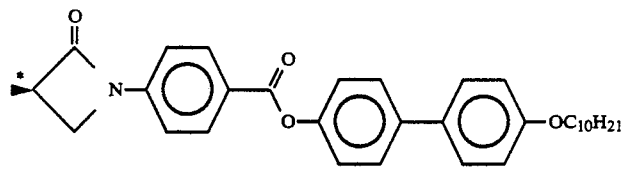

Phase sequence I 242 S$_x$* 180 X

[α]$_D^{25}$: +5.2° (c=1.2; CHCl₃)

USE EXAMPLE

In order to test the suitability of the above-described compounds as ferroelectric dopes in liquid-crystal systems having tilted smectic phases, they are admixed with test mixtures. In order to measure the polarization and the cholesteric twisting power (N*-HTP), the dopes are added to the non-chiral test mixture M1 described below in concentrations of in each case 10 mol %, and the values for the spontaneous polarization (P$_S$ in nC/cm²) and the cholesteric twisting power (HTP in μm⁻¹) of the mixture are determined.

The P$_S$ values are measured by the method of H. Diamant et al. (Rev. Sci. Instr., 28, 30, 1957). The twisting power of the cholesteric phase is determined as described, for example, in P. Kassubek et al., Mol. Cryst. Liq., Vol. 8, 305-314, 1969, in a wedge cell having an alignment layer by measuring the displacement lines under a polarizing microscope.

The twisting power of the smectic C* phase is determined by the method of selective reflection. Using a cell having a homeotropic alignment of the liquid-crystalline material, circular polarized light whose wavelength and direction of rotation in the liquid crystal matches the helix pitch and the—direction of rotation, is reflected. Since the twisting power in this smectic C* phase generally increases with decreasing temperature, observation of the temperature at which light having a wavelength of 630 nm is reflected is a direct measure of the HTP of the smectic C* phase.

In order to measure this twisting power, the dopes are added to the chiral test mixture M2 described below in concentrations of 6%. The chiral test mixture has a pitch of +0.49 μm at 6° C. If a dope having the opposite sign of the HDP is added, the twisting power drops, so that the selective reflection in the red spectral region is only observed at lower temperatures. The lower the temperature, the more negative the smectic C* twisting power of the dope.

The non-chiral test mixture M1 has the composition:

| | |
|---|---|
| 5-octyloxy-2-(4-hexoxyphenyl)pyrimidine | 25.3 mol % |
| 5-octyloxy-2-(4-butoxyphenyl)pyrimidine | 26.7 mol % |
| 5-octyloxy-2-(4-decyloxyphenyl)pyrimidine | 21.3 mol % |

-continued

| | |
|---|---|
| 5-octyloxy-2-(4-octyloxyphenyl)pyrimidine | 11.7 mol % |
| 4'-(5-decylpyrimidin-2-yl)phenyl trans-4-pentylcyclohexanecarboxylate | 15.0 mol % | and has the following liquid-crystalline phase ranges:
X 9 $S_C$ 84 $S_A$ 93 N 105 I
The chiral test mixture M2 has the composition:

| | |
|---|---|
| 5-octyl-2-(4-octyloxyphenyl)pyrimidine | 9.2 mol % |
| 5-octyloxy-2-(4-hexoxyphenyl)pyrimidine | 10.3 mol % |
| 5-octyloxy-2-(4-butoxyphenyl)pyrimidine | 11.3 mol % |
| 5-octyloxy-2-(4-decyloxyphenyl)pyrimidine | 6.2 mol % |
| 5-octyloxy-2-(4-octyloxyphenyl)pyrmidine | 3.4 mol % |
| 5-octyloxy-2-(4-dodecyloxyphenyl)pyrimidine | 6.2 mol % |
| 4'-(5-decylpyrimidin-2-yl)phenyl trans-4-pentylcyclohexanecarboxylate | 14.6 mol % |
| 4-(5-octylpyrimidin-2-yl)phenyl heptanoate | 15.3 mol % |
| (2S,3S)-2-(4-(5-octylpyrimidin-2-yl)-phenyloxy)methyl-3-butyloxirane | 9.4 mol % |
| (2S,3S)-2-(4-(5-decylpyrimidin-2-yl)-phenyloxy)methyl-3-butyloxirane | 4.7 mol % |
| (2S,3S)-2-(4-(5-dodecylpyrimidin-2-yl)-phenyloxy)methyl-3-butyloxirane | 9.4 mol % |

Table 1, columns 2 and 3, shows the values of spontaneous polarization $P_S$ and the twisting power N*HTP in the cholesteric phase obtained on addition of 10 mol % of a dope according to the invention to the mixture M1. Column 4 shows the temperature at which a mixture of 6% of the dope according to the invention and 94% of the mixture M2 reflects selectively in the red spectral region. Column 4 shows the liquid-crystalline phases of the dope. Table 2 shows, for comparison, the values for $P_S$ and HTP obtained on addition of dopes containing other chiral groups. Since the $P_S$ and HTP of the dopes depend primarily on the chiral group, and the mesogenic nucleus and the length of the side chains play only a minor role, Table 2 allows a comparison to be made with the properties of the dope according to the invention. All measurements of $P_S$ were carried out at 25° C., and the HTP was in each case measured at about 1° C. below the nematic-isotropic phase transition of the mixture.

TABLE 1

| Dope according to the invention structure | $P_S$[nC/cm²] | N*-HTP [μm⁻¹] | Selective reflection | Phases |
|---|---|---|---|---|
| [structure: $C_8H_{17}$—O—pyrimidine—phenyl—O—C(=O)—phenyl—N(CH₃)(C₈H₁₇)-azetidinone] | 26 | −7.2 | −3° C. | X 101 $S_C*$ 120.8 N* 230 I |

TABLE 2

| Comparative example | Structure | $P_s$ [nC/cm²] | N*-HTP [μm⁻¹] | Selective reflection | Phases |
|---|---|---|---|---|---|
| 2a | [$C_{12}H_{25}$—O—pyrimidine—phenyl—O—C(=O)—CH(CH₃)—CH₂—O-] | 18 | −2.7 | | X 97 I |
| 2b | [$C_8H_{17}$—O—pyrimidine—phenyl—O—C(=O)—CH—tetrahydrofuran] | 17 | +1.9 | +2° C. | X 87 I |
| 2c | [$C_{10}H_{21}$—O—phenyl—phenyl—C(=O)—O—phenyl—CH(OCH₃)—$C_9H_{19}$] | <1 | 0 | | X 40 $S_C*$ 82 $S_A*$ 108 I |
| 2d | [$C_{10}H_{21}$—O—phenyl—phenyl—O—C(=O)—phenyl—CH₂—CH—CH—$C_3H_7$ β-lactone] | <1 | 4,3 | | X 135 BP 127 I |

A comparison of the tables shows that the dope according to the invention induces a surprisingly large polarization. The use of mixtures containing dopes of this type therefore allows liquid-crystal systems with particularly fast response times to be produced. The high twisting power of the dope according to the invention can be utilized to compensate the helix of a chiral liquid-crystal mixture or alternatively to produce a short $S_C$ pitch.

Furthermore, a comparison of the tables shows that the dope according to the invention, in contrast to some comparative examples in Table 2, has a smectic C phase and a nematic phase and thus favorably affects the liquid-crystalline phase range of a mixture.

We claim:

1. An azetidinone of the formula I

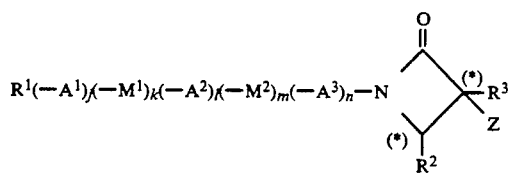

in which the symbols and indices have the following meanings:

(*) indicates a possible chiral center, $R^1$ is a straight-chain or branched alkyl radical having 1 to 16 carbon atoms, in which one or more non-adjacent —CH$_2$— groups may be replaced by —O—, —O—CO— or —CO—O—, which correspondingly reduces the number of carbon atoms in the radical, $R^2$ is a hydrogen atom or an alkyl radical having 1 to 10 carbon atoms, $R^3$ is a hydrogen atom or an alkyl radical having 1 to 10 carbon atoms, Z is H, j and l are 0, 1 or 2, k and m are 0 or 1, and n is 0, 1 or 2, with the following proviso: if j and/or l are zero, k is zero; if n is zero, m is zero; the sum of j+l+n is at least 1 and at most 3, —$A^1$ and —$A^2$ are selected from the group consisting of

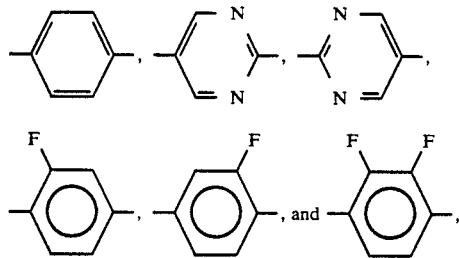

—$A^3$ is selected from the group consisting of

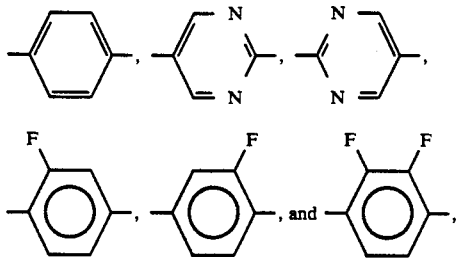

and

—$M^1$ and —$M^2$ are —O—CO— or —CO—O—.

2. An azetidinone as claimed in claim 1, $R^1$ is a straight-chain or branched alkyl radical having 6 to 12 carbon atoms, and in which one —CH$_2$— group may be replaced by —O—, or —COO—, which correspondingly reduces the number of carbon atoms in the radical, and the (—$A^1$)$_j$(—$M^1$)$_k$(—$A^2$)$_l$(—$M^2$)$_m$(—$A^3$)$_n$— group is selected from the group consisting of

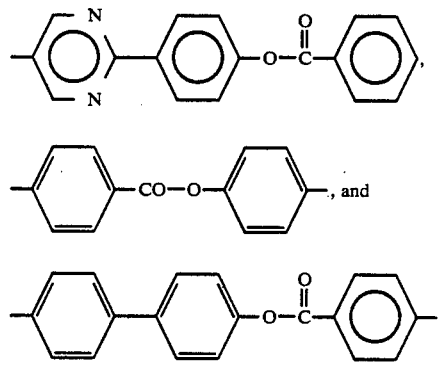

3. A liquid-crystal mixture which contains from 0.01 to 60% by weight of at least one azetidinone as claimed in claim 1.

4. A ferroelectric liquid-crystal mixture which contains from 0.01 to 60% by weight of at least one azetidinone as claimed in claim 1.

5. An electro-optical switching or display element which contains a liquid-crystal mixture as claimed in claim 3 or 4.

* * * * *